United States Patent [19]

Paul et al.

[11] Patent Number: 5,713,931
[45] Date of Patent: Feb. 3, 1998

[54] METHOD AND APPARATUS FOR DETECTING AMPLITUDE LOSS IN CARDIAC PACING PULSES

[75] Inventors: Patrick J. Paul; David Prutchi, both of Lake Jackson, Tex.

[73] Assignee: Sulzer Intermedics Inc., Angleton, Tex.

[21] Appl. No.: 700,585

[22] Filed: Sep. 16, 1996

[51] Int. Cl.$^6$ .................................................. A61N 1/37
[52] U.S. Cl. ................................................................ 607/27
[58] Field of Search .................................. 607/7, 27, 28, 607/29

[56] References Cited

U.S. PATENT DOCUMENTS

| | | | |
|---|---|---|---|
| 3,523,539 | 8/1970 | Lavezzo et al. | 607/28 |
| 4,095,603 | 6/1978 | Davies | 607/29 |
| 4,102,346 | 7/1978 | Fulker | 607/29 |
| 4,140,131 | 2/1979 | Dutcher et al. | 607/29 |
| 4,140,132 | 2/1979 | Dahl | 128/419 |
| 4,688,573 | 8/1987 | Alt | 128/419 |
| 5,076,272 | 12/1991 | Paul | 128/419 |
| 5,531,772 | 7/1996 | Prutchi | 607/17 |

*Primary Examiner*—William E. Kamm
*Attorney, Agent, or Firm*—John R. Merkling

[57] ABSTRACT

A method and apparatus for detecting loss of cardiac pacing pulse amplitude includes a comparator for comparing the actual pulse voltage to a reference voltage. In one advantageous embodiment, the reference voltage is determined as a percentage of the programmed pulse amplitude. The comparison of the reference voltage and the actual voltage is latched at the time when a pulse is actually created to produce a signal indicative of whether the amplitude of the actual pulse exceeds the reference. When the amplitude falls below the reference, the system may take corrective action.

11 Claims, 2 Drawing Sheets

METHOD AND APPARATUS FOR DETECTING AMPLITUDE LOSS IN CARDIAC PACING PULSES

TECHNICAL FIELD

Our invention relates cardiac stimulators and particularly to such stimulators that produce cardiac pacing pulses.

BACKGROUND OF OUR INVENTION

Implanted cardiac pacemakers are employed to assist patients suffering from severe bradycardia or chronotropic incompetence. A cardiac pacemaker captures the heart by delivering an electrical pulse to the myocardium of a selective heart chamber during an interval in the cardiac cycle in which the cardiac tissue is excitable. The electrical pulses cause depolarization of cardiac cells and consequently, contraction of the chamber, provided that the energy of the pacing pulse, as delivered to the myocardium, exceeds a threshold value.

Though implanted pacemakers are generally very reliable, it is still necessary to periodically replace the battery in these pacemakers. However, battery life is a function of a number of characteristics including pacing rate and pulse amplitude and therefore can not be determined with absolute certainty.

Many patients and their physicians would prefer to forestall the replacement of the pacemaker battery for the longest possible period. This is because the pacemaker must be replaced at the end of battery life through a surgical procedure. Thus, the physician may decide in some circumstances to attempt to extend battery life by adjusting the pacing rate or pulse amplitude.

Some implantable pacemakers include indicators which advise the physician of the extent of the remaining battery life. For example, the Relay® brand pacemakers distributed by the assignee of the present application, provide two indicators of impending end of battery life. The first indicator, called the intensified follow-up indicator (IFI), causes a dual chamber rate adaptive pacemaker to shift to a single chamber asynchronous non-rate adaptive pacing at 90 pulses per minute in a magnet mode. The magnet mode is implemented by operating a reed switch using an external magnet. Generally, this indicator simply means that closer monitoring of battery life would be appropriate. The next indicator that the patient would encounter is called the elective replacement indicator (ERI). In this case there is a shift to non-triggered, single chamber, non-rate adaptive pacing at the programmed rate in the non-magnet mode and a single chamber asynchronous non-rate adaptive pacing at a pace rate of 80 pulses per minute in the magnet mode. At this indicator, it would be recommended that the pulse generator be replaced or reprogrammed since the battery is close to the end of service voltage at the current programmed parameters. Generally the end of service of the battery will follow the elective replacement indicator in three to six months.

Patients and their physicians may wish to push the margin with respect to end of battery service. However, a number of pacing parameters may tend to change progressively from the programmed parameters near end of battery life. For example, the pulse amplitude will be reduced because of the inability to recharge tank capacitors within the time available between consecutive pacing pulses at a given pacing rate.

Obviously, pulses of sufficiently reduced output amplitude may be insufficient to capture the heart muscle of the chamber under stimulation. On the extreme, the patient's life could be endangered, and in many other instances the efficacy of the pacing may be compromised by diminished pulse amplitude.

Physicians typically program implantable cardiac pacemakers to produce pulses with an amplitude and duration which exceed the capture threshold value by an acceptable safety margin. As the battery of the implantable device is depleted, however, its internal impedance increases. Thus it becomes increasingly more difficult for tank capacitors to be effectively recharged to the programmed value in time for delivery of the next pacing pulse.

The situation worsens if the desired pulse amplitude, pulse width, or pacing rate increase. This is especially problematic in rate responsive pacemakers, since pulse amplitude may drop below the capture threshold as the device automatically increases the pacing rate in response to patient exercise. Under these conditions, the patient may be placed at risk since pacing support may fall at a time when the patient's organs have an increased need for blood supply.

Thus, it would be highly desirable to have a cardiac stimulation device which monitors pulse amplitude and takes appropriate corrective action when problems are detected.

SUMMARY OF OUR INVENTION

We have invented a system for monitoring the amplitude of pacing pulses produced by implantable cardiac pacemakers. When the detected amplitude falls below a threshold level, appropriate corrective action may be taken. For example, the device's mode of operation could be switched to compensate for increased demand while maintaining the patient under safe pacing conditions.

In accordance with one embodiment of our invention, rather than using a fixed voltage as a threshold for comparison, the actual amplitude is compared to the programmed amplitude thereby enabling detection of sufficiently altered conditions to require corrective action. For example, when the actual amplitude falls below a given percentage of the programmed amplitude, corrective action can be implemented.

In one implementation of the present invention, the actual pulse amplitude is compared to a programmed pulse amplitude scaled by a voltage divider which produces a signal for comparison which is a fixed percentage of the target value. When the actual pulse amplitude is less than the scaled target potential under the given programmed conditions, corrective action is initiated.

DETAILED DESCRIPTION OF OUR PREFERRED EMBODIMENTS

We will now describe the preferred embodiment of our invention with reference to the accompanying figures. Like numerals will be used to designate like parts throughout.

Figure 1:
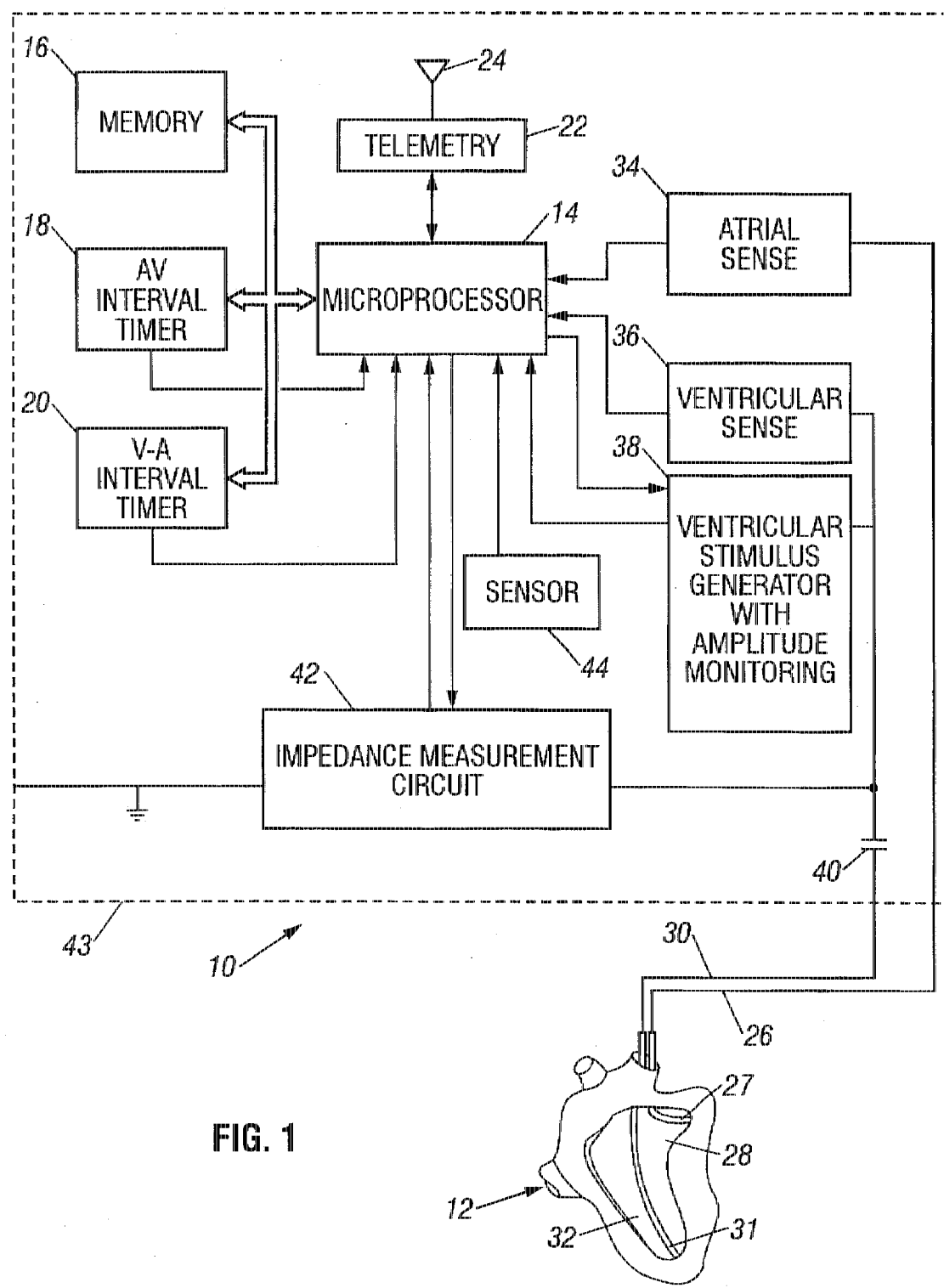
FIG. 1 is a block diagram of a pacemaker according to an embodiment of our invention.

Referring now to FIG. 1, a pacemaker, generally designated 10, is illustrated in schematic fashion with connection to a human heart 12. For ease of illustration, we have elected to describe our invention in connection with a pacemaker having atrial sensing and ventricular sensing and pacing. It should be understood, however, that our invention can be employed in connection with an apparatus for sensing in the atrium, the ventricle or both and that both atrial or ventricular pacing or either of them could be provided without departing from the teachings of our invention. Our invention could also be implemented in an apparatus that includes an implantable defibrillator/cardioverter.

With this understanding, the illustrated pacemaker 10 comprises a microprocessor 14 which executes various control programs to regulate the action of the pacemaker. The microprocessor 14 is connected to additional memory 16 for the storage of programs and data as may be needed. As is known in the art, one or more internal clocks may be provided to permit timing of various events. For example, an A-V interval timer 18 may be provided. Similarly, a V-A interval timer 20 may also be provided, as known in the art. The microprocessor is provided with a telemetry circuit 22 to enable communication, across an antenna 24, with an external programmer (not shown). Telemetry permits an attending physician to obtain data and information from the pacemaker and to set various selectable pacemaker control parameters, as known in the art.

The pacemaker 10 is connected to the heart 12 through a first lead 26 to an electrode 27 in the atrium 28 and through a second lead 30 to an electrode 31 in the ventricle 32. An indifferent electrode (e.g., the pacemaker can) is provided to complete the electrical circuit through the body. In the illustrated embodiment, a can or outer casing 43 of the pacemaker serves as the indifferent electrode. Bipolar leads can also be used with our invention as well as the unipolar leads illustrated here.

Atrial electrogram sensing, through an atrial sense circuit 34, and ventricular sensing, through a ventricular sense circuit 36, provide information to the microprocessor concerning the condition and responsiveness of the heart. In addition, pacing pulses are provided to the ventricle from a ventricular stimulus generator 38. It is clearly within the scope of those skilled in the art to provide cardioversion/defibrillation capabilities in response to the detected condition of the heart. Stimulation to the heart is passed through a coupling capacitor 40.

To control the pulse rate of the ventricular stimulus generator 38, the microprocessor 14 acquires information on the condition of the heart through an impedance circuit 42. The impedance circuit 42 detects changes in impedance, for example, due to the changing shape of the heart as it beats and pumps blood. This information can be used to derive a measure of the stroke volume or ejection fraction or end diastolic volume of the heart. Furthermore, the shape of the impedance waveform can provide information on other cardiac timing parameters such as isovolumetric contraction time or pre-ejection period.

Sensor 44 may also be provided to obtain an indication of physiologic need and to adjust the pacing rate. Such a sensor may be an accelerometer, as described by Dahl, U.S. Pat. No. 4,140,132, (incorporated herein by reference) a temperature sensor, as described by Alt, U.S. Pat. No. 4,688,573 (also incorporated herein by reference), or any other suitable sensor of a parameter which may be correlated to physiologic need of the patient.

Figure 2:
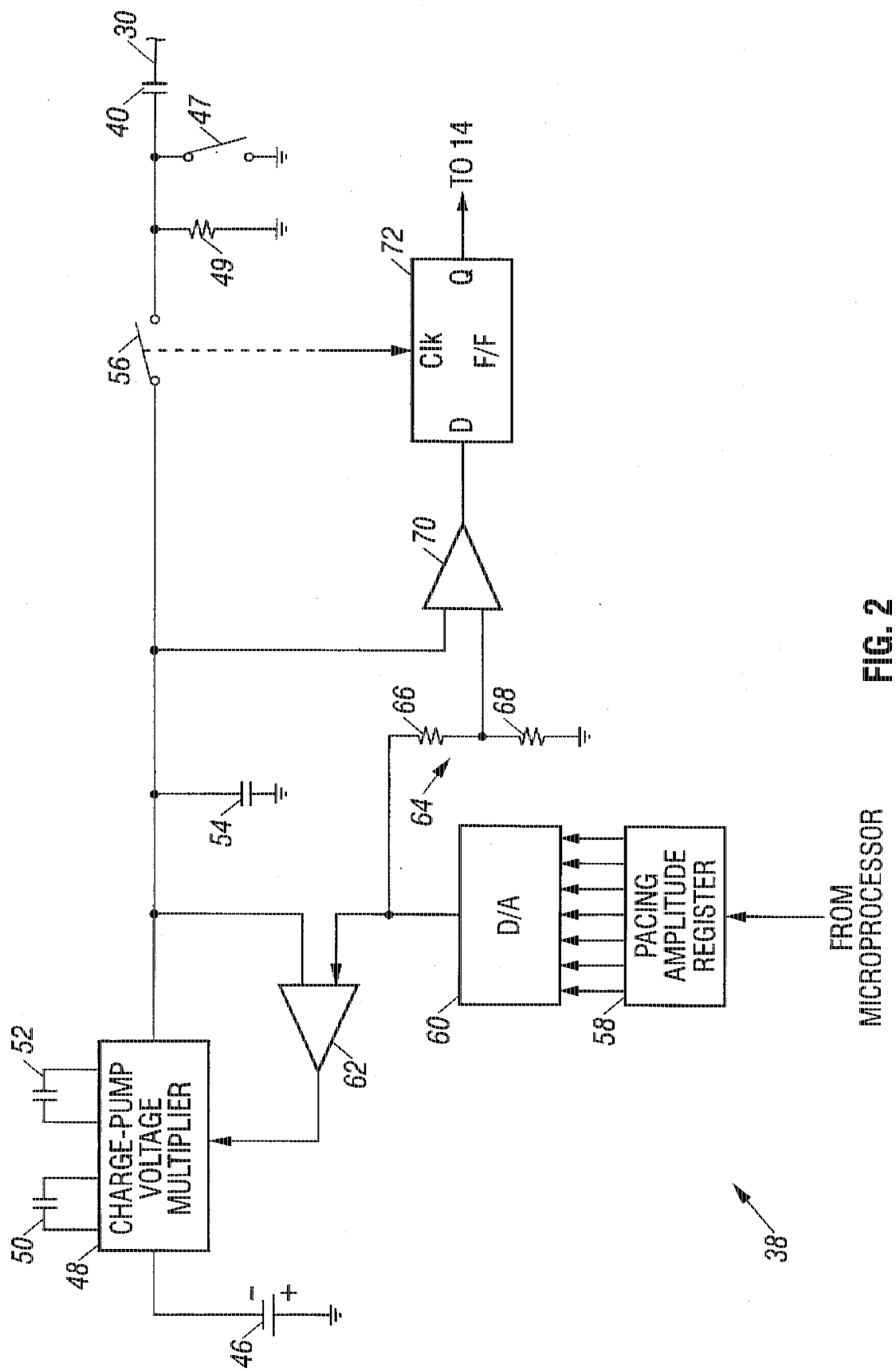
FIG. 2 is a circuit diagram showing a ventricular stimulus generator with monitoring in accordance with our invention.

The ventricular stimulus generator 38, shown in FIG. 2, includes a battery 46 connected to charge-pump voltage multiplier 48. The charge-pump voltage multiplier 48 includes two pump capacitors 50 and 52. The charge-pump voltage multiplier 48 charges the tank capacitor 54. A switch 56 connects the tank capacitor 54 to the heart 12 through a coupling capacitor 40. A switch 47 and resistor 49 may be used to discharge the coupling capacitor 40.

A pacing amplitude register 58 stores a programmed pacing amplitude received from the microprocessor 14. The pacing amplitude may be set by the physician in order to provide appropriate treatment for a particular patient. The amplitude stored in the pacing amplitude register 58 is converted to an analog signal by the digital-to-analog converter 60. This signal is then compared by comparator 62 with the voltage across tank capacitor 54. The output is provided to the control input of the charge-pump voltage multiplier 48. As a result, the charge-pump voltage multiplier 48 provides that amount of voltage multiplication necessary to produce a pacing pulse which corresponds to the pre-programmed pacing amplitude.

When the tank capacitor 54 is charged to a voltage that exceeds the target voltage set by the pacing amplitude register 58, the comparator 62 flips its state and the pumping action of the charge-pump voltage multiplier 48 is terminated. Beyond this point, the charge-pump voltage multiplier 48 is controlled in such a way that the voltage of the tank capacitor 54 is maintained just above the value set by the register 58. When the capacitor 54 is discharged to produce a pacing pulse, the charge-pump voltage multiplier 48 is again put into action to "top-off" the tank capacitor 54.

The analog signal of the programmed pulse amplitude, produced by the digital to analog converter 60, is scaled by a voltage divider 64 which includes a pair of resistors 66 and 68. The voltage divider 64 produces a voltage signal which is preset percentage of the programmed pulse amplitude. For example, in one advantageous embodiment, the output of the voltage divider 64 is about 90% of the programmed pulse amplitude. The output of the voltage divider 64 is then connected to the input of a comparator 70. The other input to the comparator 70 is taken from the output of the tank capacitor 54.

The comparator 70 is connected to a flip-flop 72. The flip-flop 72 is clocked by a signal indicative of the state of closure of the switch 56. That is, the flip-flop 72 only latches an input signal when the switch 56 is being closed. As a result, the only time there is a change in the output from the flip-flop 52 is when there has been a pulse produced by the tank capacitor 54. Thus, the output state of the flip-flop 72 is a result of the comparison between the actual amplitude of the pacing pulses produced by the tank capacitor 54 and the signal from the voltage divider 64 which is a percentage of the preprogrammed target amplitude. The flip-flop 72 may indicate a high signal when the actual amplitude is greater than the target voltage set by the voltage divider 64 and a low signal when the actual amplitude falls below the target voltage set by the voltage divider 64.

The output of the flip-flop 72 is communicated to the microprocessor 14 which determines the appropriate action to take in accordance with preprogrammed instructions. In response to a low signal, the microprocessor can switch the operation of the pacemaker 10 to adjust for the diminished battery capacity. For example, the pacing rate could be decreased, the rate adaptive feature could be suspended, non-essential features could be turned off, or any combination of these actions could be implemented. It is also possible to modify the operating mode of the charge-pump voltage multiplier 48 in order to compensate for the increased charge demand.

In addition, the patient may be given a physically perceptible warning that lower amplitude pulses are being produced. This can be done, for example, by producing pacing pulses which cause the patient to twitch, as disclosed for example, in U.S. Pat. No. 5,076,272 to Paul, hereby expressly incorporated by reference herein.

When pacing pulses issued from the tank capacitor 54 exceed the target value set by the voltage divider 64, the comparator 70 flips its state and the normal operation of the pacemaker may continue using the current mode of operation.

Our invention may be embodied in other specific works without departing from the spirit or essential characteristics thereof. The foregoing description, is, therefore, to be viewed in all respects as illustrative and not restrictive. The scope of our invention is defined by the appended claims.

We claim as our invention:

1. An implantable cardiac stimulation apparatus comprising:

an implantable outer casing containing
      a battery;
      a pulse generator connected to said battery for producing pacing pulses, said pulse generator comprising a tank capacitor charged from said battery and a switch connected to said tank capacitor for controlling delivery of said pacing pulses;
      means for producing a reference voltage;
      a comparator, connected to said tank capacitor and said means for producing a reference voltage, said comparator comparing the voltage amplitude of said pacing pulses with said reference voltage; and
      a detector for indicating the state of said comparator at a selected time;
   a circuit coupled to said switch for enabling said detector as said switch is closed; and
   means for altering production of said pacing pulses by said pulse generator in response to said detector.

2. The apparatus of claim 1 including means connected to said pulse generator for selecting a pulse amplitude for said pacing pulses and wherein said means for producing a reference voltage produces a reference voltage which is a percentage of the selected pulse amplitude.

3. The apparatus of claim 2 wherein said means for producing said reference voltage is a voltage divider.

4. The apparatus of claim 1 including a device for changing the pacing rate in response to the detection of a pacing pulse having an amplitude below the reference voltage.

5. The apparatus of claim 1 further comprising
   means for detecting a parameter correlated to physiologic need of a patient;
   means for adapting a pacing rate to said detected parameter and
   means for disregarding said rate adaptive means when the amplitude of a pacing pulse falls below the reference voltage.

6. A method for stimulating a patient's heart comprising the steps of:
   producing a train of pacing pulses by charging a tank capacitor from a battery and discharging said capacitor across a switch into the patient's heart;
   detecting the amplitude of said pacing pulses as said switch is closed; and
   producing a signal indicative of whether the amplitude of said pacing pulses corresponds to a desired pacing pulse amplitude; and
   altering said train of pacing pulses in response to said signal.

7. The method of claim 6 including the step of setting said desired pulse amplitude.

8. The method of claim 7 wherein the step of producing a signal includes the step of producing a scaled pulse amplitude signal which is a percentage of the desired pulse amplitude and comparing said scaled pulse amplitude signal to the amplitude of said pacing pulse.

9. The method of claim 1 including the step of reducing the pacing rate when said pulse amplitude falls below the desired pulse amplitude by a predetermined amount.

10. The method of claim 1 further comprising
    detecting a parameter correlated to physiologic need;
    adjusting the pacing rate in response to said detected parameter; and
    terminating said adjusting of the rate of the pacing when the amplitude of the pacing pulse falls below the desired pulse amplitude by a predetermined amount.

11. The method of claim 6 further comprising the step of giving the patient a patient perceptible stimulus when the amplitude of the pacing pulse falls below the desired pulse amplitude by a predetermined amount.

* * * * *